(12) United States Patent
Nishikawa et al.

(10) Patent No.: US 10,842,790 B2
(45) Date of Patent: Nov. 24, 2020

(54) IMMUNOPOTENTIATOR POTENTIATING TUMOR IMMUNITY OR INFECTION IMMUNITY

(71) Applicant: Osaka University, Osaka (JP)

(72) Inventors: Hiroyoshi Nishikawa, Osaka (JP); Shimon Sakaguchi, Osaka (JP); Atsushi Tanaka, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/326,183

(22) PCT Filed: Jul. 16, 2015

(86) PCT No.: PCT/JP2015/070418
§ 371 (c)(1),
(2) Date: Jan. 13, 2017

(87) PCT Pub. No.: WO2016/010114
PCT Pub. Date: Jan. 21, 2016

(65) Prior Publication Data
US 2017/0216288 A1    Aug. 3, 2017

(30) Foreign Application Priority Data
Jul. 16, 2014    (JP) ................. 2014-146031

(51) Int. Cl.
*A61K 31/06* (2006.01)
*A61K 31/506* (2006.01)
*A61K 45/06* (2006.01)
*G01N 33/574* (2006.01)

(52) U.S. Cl.
CPC ............. *A61K 31/506* (2013.01); *A61K 45/06* (2013.01); *G01N 33/57426* (2013.01); *G01N 2333/4703* (2013.01); *G01N 2333/70514* (2013.01); *G01N 2333/70589* (2013.01); *G01N 2800/52* (2013.01)

(58) Field of Classification Search
CPC .................................. A61K 31/506
USPC .................................. 514/252.18
See application file for complete search history.

(56) References Cited

U.S. PATENT DOCUMENTS

| 6,156,305 A * | 12/2000 | Brauker ............... A61K 9/0024 424/93.2 |
| 8,481,029 B2 * | 7/2013 | Glennie ................ A61P 19/02 424/130.1 |
| 2013/0190251 A1 | 7/2013 | Witko-Sarsat et al. | | |

FOREIGN PATENT DOCUMENTS

| JP | 2013-522613 A | | 6/2013 | |
| WO | WO 2004/026311 | * | 1/2004 | .......... A61K 31/506 |
| WO | WO 2004/026311 A2 | | 4/2004 | |
| WO | WO 2011113942. | * | 9/2011 | .......... A61K 31/506 |

OTHER PUBLICATIONS

Larmonier et al Journal of Immunology, 2008, 181(10), 6955-6953.*
Larmonier et al. Journal of Immunology, Nov. 15, 2008, vol. 181, No. 10, pp. 6955-6963.*
Zitvogel et al. Journal of clinical oncology:American Society of Clinical Oncology (2005), 23(16) 2516.*
Slike et al. Stem Cells, Sep. 2005, vol. 23, No. 8, pp. 1082-1088, Ma.*
Zitvogel, Nature Reviews Clinical Oncology (2016), 13(7), 431-.*
Maruyama et al. Proceedings of the Japanese Cancer Association, Aug. 15, 2005, vol. 64, pp. 492-493.*
Dagmar et al. Blood, Nov. 16, 2006, vol. 108, No. 11, part 1, pp. 623A-624A.*
Zitvogel et al. Journal of clinical oncology : official journal of the American Society of Clinical Oncology (2005), 23(16_suppl), 2516.*
Zhang, Nature Genetics vol. 44 | No. 8 | Aug. 2012, 861-872.*
Li et al. Cancer Cell International 2012, 12:52.*
Balachandran, Nature Medicine, 2011, 17(9), 1094-1101, Cai, Clin Cancer Res; 2012,.18(20), 5761-5772.*
Appel, et al. 2005 "Effects of imatinib on normal hematopoiesis and immune activation" *Stem Cells* 23(8): 1082-1088.
Baccarani et al. 2006 "Evolving concepts in the management of chronic myeloid leukemia: recommendations from an expert panel on behalf of the European LeukemiaNet" *Blood* 108: 1809-1820.
Bund, et al. 2006 "Immunomodulatory effects of ST1571 in chronic myeloid leukaemia" *Blood* 108(11): 623A-624A (Abstract 2129), in 4 pages.
International Search Report in International Application No. PCT/JP2015/070418, dated Aug. 18, 2015.
Larmonier, et al. 2008 Imatinib mesylate inhibits CD4+ CD25+ regulatory T cell activity and enhances active immunotherapy against BCR-ABL− tumors *Journal of Immunology* 181(10): 6955-6963.
Maruyama, et al. "STI571 (Glivec) ni yoru NK izonsei Koshuyo Koka no Yudo" *Proceedings of the Japanese Cancer Association* 64: 492-493, Abstract PA3-1207.
Sugiyama et al. 2013 "Anti-CCR4 mAb selectively depletes effector-type FoxP3+CD4+ regulatory T cells, evoking antitumor immune responses in humans" *Proc Natl Acad Sci* 110: 17945-17950.

* cited by examiner

*Primary Examiner* — Nizal S Chandrakumar
(74) *Attorney, Agent, or Firm* — Knobbe, Martens, Olson & Bear, LLP

(57) ABSTRACT

An object of the present invention is to provide an immunopotentiating agent for reducing Tregs (in particular, effector Tregs) and potentiating tumor immunity or infection immunity. Imatinib and/or a salt thereof has the action of reducing Tregs (in particular, effector Tregs) and potentiating tumor immunity or infection immunity, and can be used as an active ingredient for the immunopotentiating agent.

4 Claims, 11 Drawing Sheets

IMMUNOPOTENTIATOR POTENTIATING TUMOR IMMUNITY OR INFECTION IMMUNITY

TECHNICAL FIELD

The present invention relates to an immunopotentiating agent for potentiating tumor immunity or infection immunity. More specifically, the present invention relates to an immunopotentiating agent for reducing regulatory T cells and potentiating tumor immunity or infection immunity. The present invention also relates to a testing method for predicting therapeutic efficacy in a patient with chronic myelogenous leukemia receiving administration of imatinib and/or a salt thereof.

BACKGROUND ART

Immune responses such as antibody production responses are defense mechanisms possessed by an organism for eliminating foreign substances such as microorganisms. On the other hand, an organism also possesses mechanisms of immune tolerance for preventing immune responses against self-derived antigens to avoid self-damage caused by immune responses. Immune tolerance is broadly classified into the two mechanisms, i.e., central tolerance and peripheral tolerance, and peripheral tolerance is mediated by $CD4^+$ regulatory T cells (Tregs).

It has been revealed that Tregs suppress not only autoimmunity, but also exogenous antigen-induced inflammation, allergic diseases, organ transplant rejections, and the like. On the other hand, it is known that Tregs also have suppressive action on tumor immunity or infection immunity, and rather act to diminish therapeutic effects against tumors or infections.

Tumor immunotherapy has conventionally attracted attention as a therapy useful for use in combination with chemotherapy or the like, or for treating tumors untreatable with surgical therapy. In tumor immunotherapy, however, suppression of Tregs is an important issue. In particular, effector Tregs showing $CD45RA^-FOXP3^{high}CD4^+$ are known to exhibit strong immunosuppressive action, have a typical Treg characteristic such as producing only small amounts of cytokines, and also to be abundant in tumor sections (see Non Patent Literature 1). Thus, it is particularly important to reduce effector Tregs in tumor immunotherapy. Various approaches for depleting Tregs or inhibiting the suppressive activity of Tregs have been previously attempted; however, no technology for sufficiently suppressing Tregs has been developed yet. Moreover, because immunity plays a significant role against infections, reducing Tregs and potentiating infection immunity in immunosuppressed patients with infections is extremely important in establishing immunotherapy for infections.

With such prior art in the background, the development of an immunopotentiating agent for reducing Tregs (in particular, effector Tregs) and potentiating tumor immunity or infection immunity is eagerly desired.

On the other hand, imatinib and/or a salt thereof is a tyrosine kinase inhibitor that targets the gene product Bcr-Abl of the Philadelphia chromosome, and is used in the treatment of patients with chronic myelogenic leukemia, Philadelphia chromosome-positive acute lymphatic leukemia, KIT (CD117)-positive gastrointestinal stromal tumor, and the like. Effects of imatinib upon the immune system, however, have not been fully elucidated yet.

For determination of the therapeutic effect of chronic myelogenous leukemia, a guideline is known in which, from a molecular genetic standpoint, 100,000 to 1,000,000 cells contained in peripheral blood are classified into the state where leukemic cells bearing Bcr-Abl gene do not remain, i.e., complete molecular response (CMR), and the state where leukemic cells bearing Bcr-Abl gene remain, i.e., non-complete molecular response (Non-CMR) (see Non Patent Literature 2). Although imatinib and/or a salt thereof has produced a dramatic clinical effect against chronic myelogenous leukemia, CMR has been achieved in only approximately half of patients, and factors that make such a difference between CMR and Non-CMR are unknown.

CITATION LIST

Non Patent Literature

Non Patent Literature 1: Daisuke Sugiyama et al., PNAS Early Edition, www.pnas.org/cgi/doi/10.1073/pnas.1316796110

Non Patent Literature 2: Baccarani M. et al., Blood. 2006; 108: 1809-1820

SUMMARY OF INVENTION

Technical Problem

An object of the present invention is to provide an immunopotentiating agent for reducing Tregs (in particular, effector Tregs) and potentiating tumor immunity or infection immunity. Another object of the present invention is to provide a testing method for predicting therapeutic efficacy in a patient with chronic myelogenous leukemia receiving administration of imatinib and/or a salt thereof.

Solution to Problem

The present inventors made analysis on immune responses in CMR patients and Non-CMR patients with chronic myelogenous leukemia who received administration of imatinib mesylate, and consequently found that the CMR patients showed a reduction in Tregs (in particular, effector Tregs) and potentiation of the tumor immune response (in particular, $CD8^+$ killer T cell) activity. The inventors also found that the reduction in Tregs caused by imatinib mesylate is not attributed to blockade of the kinase activity of Bcr-Abl gene, which is the target molecule of imatinib, but is attributed to off-target action, which is lymphocyte-specific protein tyrosine kinase (LCK)-inhibitory action.

Furthermore, in order to apply the reduction in Tregs caused by imatinib mesylate to tumor immunotherapy, the present inventors added imatinib mesylate into human peripheral blood to induce cancer antigen- or viral antigen-specific $CD8^+$ T cells, and consequently found that this resulted in a reduction in Tregs and potentiation of cancer antigen- or viral antigen-specific $CD8^+$ T cell induction, compared to a group without the addition of imatinib mesylate.

The present inventors conducted further research based on these findings, thereby completing the present invention. Specifically, the present invention provides aspects of invention as listed below.

Item 1. An immunopotentiating agent for potentiating tumor immunity or infection immunity, the immunopotentiating agent comprising imatinib and/or a salt thereof as an active ingredient.

Item 2. The immunopotentiating agent according to item 1, which is used for potentiating tumor immunity in treating a tumor.

Item 3. The immunopotentiating agent according to item 1 or 2, which is used for potentiating tumor immunity in treating solid cancer.

Item 4. The immunopotentiating agent according to item 1, which is used for potentiating infection immunity in preventing or treating an infection.

Item 5. An agent for suppressing regulatory T cells comprising imatinib and/or a salt thereof as an active ingredient.

Item 6. The agent for suppressing regulatory T cells according to item 5, which is used for suppressing effector regulatory T cells.

Item 7. Use of imatinib and/or a salt thereof for manufacture of an immunopotentiating agent for potentiating tumor immunity or infection immunity.

Item 8. A method for potentiating tumor immunity or infection immunity comprising the step of administering an effective amount of imatinib and/or a salt thereof to an individual in need of potentiation of tumor immunity or infection immunity.

Item 9. Imatinib and/or a salt thereof used in treatment for potentiating tumor immunity or infection immunity.

Item 10. A testing method for predicting therapeutic efficacy in a patient with chronic myelogenous leukemia receiving administration of imatinib and a salt thereof, the method comprising:

counting regulatory T cells contained in peripheral blood collected from the patient with chronic myelogenous leukemia receiving administration of imatinib and/or a salt thereof, and predicting therapeutic efficacy of imatinib and/or a salt thereof for chronic myelogenous leukemia based on the number of the regulatory T cells.

Item 11. The testing method according to item 10, wherein effector regulatory T cells contained in the peripheral blood are counted, and the therapeutic efficacy of imatinib and/or a salt thereof for chronic myelogenous leukemia is predicted based on the number of the effector regulatory T cells.

Item 12. The testing method according to item 10, or 11, wherein the testing method is for predicting whether a molecular genetic complete response will be achieved or not.

Item 13. A biomarker for predicting therapeutic efficacy in a patient with chronic myelogenous leukemia receiving administration of imatinib and/or a salt thereof, the biomarker comprising regulatory T cells contained in peripheral blood.

Item 14. A testing kit for predicting therapeutic efficacy in a patient with chronic myelogenous leukemia receiving administration of imatinib and/or a salt thereof, the testing kit comprising a reagent for detecting regulatory T cells contained in peripheral blood.

Advantageous Effects of Invention

The immunopotentiating agent of the present invention can reduce Tregs (in particular, effector Tregs) and potentiate tumor immune responses, and thus, can bring benefits to tumor-bearing patients receiving immunotherapy. The immunopotentiating agent of the present invention can also reduce Tregs (in particular, effector Tregs) and potentiate infection immunity, and thus, can enhance the effect of preventing or treating infections. Furthermore, the immunopotentiating agent of the present invention uses imatinib and/or a salt thereof, which has been previously put in clinical use, and of which security has been confirmed, and thus, has the advantage of having a low barrier to clinical applications.

Furthermore, the testing method of the present invention can estimate whether CMR can be achieved or not in a patient with chronic myelogenous leukemia receiving the administration of imatinib and/or a salt thereof, and predict the therapeutic efficacy of imatinib and/or a salt thereof. This allows a determination to be made as to whether imatinib and/or a salt thereof should be administered or not, and allows an appropriate therapeutic strategy for chronic myelogenous leukemia to be made.

DESCRIPTION OF EMBODIMENTS

1. Immunopotentiating Agent

Figure 1:
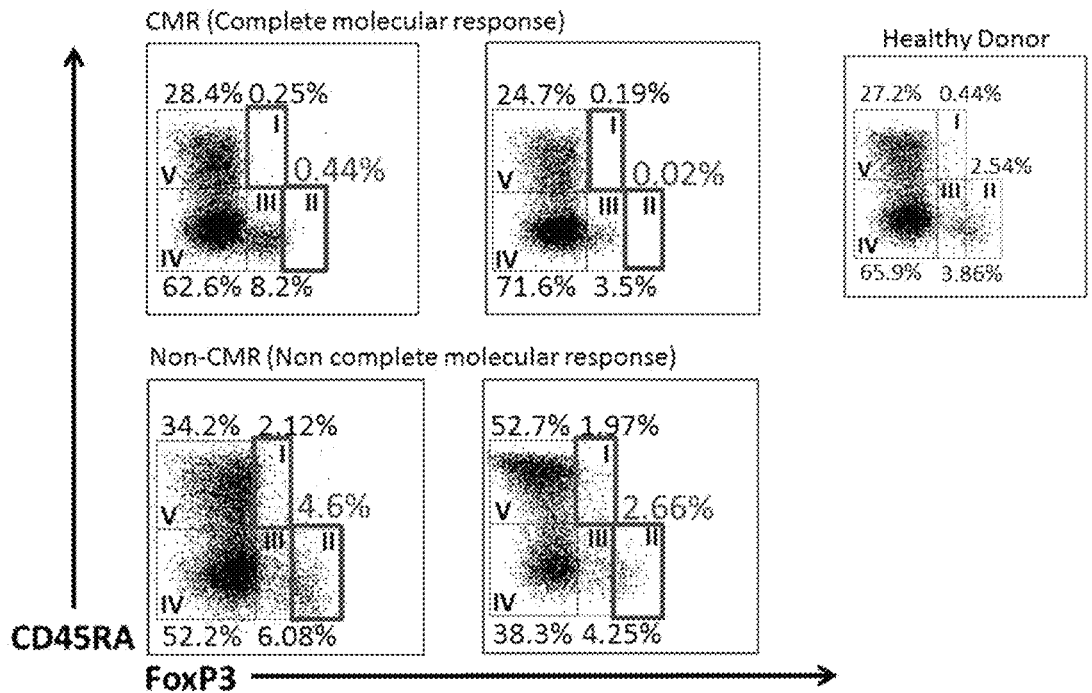
FIG. 1 shows the results of measurement of CD45RA and FoxP3 expression levels for CD4-positive cells derived from the peripheral blood of representative two CMR patients, two Non-CMR patients, and one healthy donor in Test Example 1.

The immunopotentiating agent of the present invention is an immunopotentiating agent used for potentiating tumor immunity or infection immunity, which comprises imatinib and/or a salt thereof as an active ingredient. Hereinafter, the immunopotentiating agent of the present invention will be described in detail.

[Active Ingredient]

The immunopotentiating agent of the present invention uses imatinib and/or a salt thereof as the active ingredient. Imatinib is a compound that has been previously used as a molecular target drug that targets Bcr-Abl, and is a known compound also denoted as 4-(4-methylpiperazin-1-ylmethyl)-N-[4-methyl-3-(4-pyridin-3-yl)pyrimidin-2-ylamino) phenyl]-benzamide.

While the salt of imatinib is not particularly limited as long as it is a pharmacologically acceptable salt, examples thereof include organic sulfonic acid salts, organic carboxylic acid salts, and inorganic acid salts. Specific examples of organic sulfonic acid salts include acid addition salts with mesylic acid (methanesulfonic acid), ethanesulfonic acid, 2-hydroxyethanesulfonic acid, benzenesulfonic acid, p-toluenesulfonic acid, naphthalene-2-sulfonic acid, and the like. Specific examples of organic carboxylic acid salts include acid addition salts with trifluoroacetic acid, acetic acid, propionic acid, glycolic acid, succinic acid, maleic acid, fumaric acid, hydroxymaleic acid, malic acid, tartaric acid, citric acid, arginine, lysine, benzoic acid, 2-phenoxy-benzoic acid, 2-acetoxy-benzoic acid, salicylic acid, 4-aminosalicylic acid, mandelic acid, cinnamic acid, nicotinic acid, isonicotinic acid, and the like. Specific examples of inorganic acid salts include acid addition salts with hydrochloric acid, sulfuric acid, phosphoric acid, and the like. These salts of imatinib may be used alone or in combination of two or more.

The immunopotentiating agent of the present invention may use either imatinib or a salt thereof, or may use a combination of imatinib and a salt thereof, as the active ingredient. Among imatinib and salts thereof, an organic sulfonic acid salt of imatinib, in particular, the mesylate salt of imatinib, which has high safety, and has been previously put in clinical use, is suitably used as the active ingredient of the immunopotentiating agent of the present invention.

[Targets for Application]

The immunopotentiating agent of the present invention is used for potentiating tumor immunity or infection immunity. The subject to which the immunopotentiating agent of the present invention is applied is not particularly limited as long as it is a subject in need of potentiation of tumor immunity or infection immunity, and may be a human, as well as a non-human mammalian such as a dog, a cat, a rabbit, a guinea pig, a mouse, a rat, a cow, or a monkey.

Specifically, in the field of tumors, the immunopotentiating agent of the present invention can reduce Tregs (in particular, effector Tregs) and potentiate the antitumor immunity (in particular, CD8$^+$ killer T cell) activity in cancer patients, and thus, can enhance the therapeutic effect of tumors. The cancer patient to which the immunopotentiating agent of the present invention is applied may be a patient receiving any of immunotherapy, surgical therapy, radiotherapy, and a combination thereof. The immunopotentiating agent of the present invention, however, is suitably used in a tumor-bearing patient receiving immunotherapy, because the potentiation of the antitumor immunity activity is strongly required in immunotherapy.

While the type of the immunotherapy being received by the tumor-bearing patient to which the immunopotentiating agent of the present invention is applied is not particularly limited, examples thereof include non-specific immunotherapy such as lymphokine-activated killer cell therapy, cancer antigen-specific T-cell receptor-transduced T-cell therapy, chimeric antibody-transduced T-cell therapy, tumor tissue-infiltrating lymphocyte therapy, or dendritic cell therapy; cancer vaccine therapy using a tumor cell vaccine, a cancer-specific antigen peptide, or the like; cytokine therapy using interleukin-2, interleukin-12, interferon-α, tumor necrosis factor, or the like; antibody therapy against immune checkpoint molecules; and gene therapy using a gene involved in antitumor immunity.

While the tumor to which the immunopotentiating agent of the present invention is applied is not particularly limited, examples thereof include blood malignant tumors such as chronic myelogenous leukemia, acute myelogenous leukemia, chronic lymphatic leukemia, acute lymphatic leukemia, myeloma, and malignant lymphoma; and solid tumors such as lung cancer, breast cancer, gastric cancer, liver cancer, colorectal cancer, colon cancer, rectal cancer, tongue cancer, thyroid cancer, renal cancer, pancreatic cancer, prostatic cancer, endometrial cancer, ovarian cancer, bladder cancer, cervical cancer, bile duct cancer, gallbladder cancer, oral cancer, malignant melanoma, neuroblastoma, osteosarcoma, chondrosarcoma, rhabdomyosarcoma, and leiomyosarcoma. Among these tumors, solid cancer may be preferred.

In the field of infections, specifically, the immunopotentiating agent of the present invention is administered for preventing or treating an infection, in order to reduce Tregs (in particular, effector Tregs) and potentiate infection immune responses in an individual in need of prevention or treatment of an infection. More specifically, when the immunopotentiating agent of the present invention is used for preventing an infection, it may be administered with a vaccine for an infection. This allows a reduction in Tregs to enhance the expression of infection immune responses elicited by the vaccine for an infection. When the immunopotentiating agent of the present invention is used for treating an infection, it may be administered alone or with a therapeutic drug for an infection. This allows a reduction in Tregs and potentiation of infection immunity, which allows the infection to be improved or cured.

The infection to which the immunopotentiating agent of the present invention is applied may be any of viral infections, bacterial infections, fungal infections, and the like, and examples thereof include influenza, hepatitis, tuberculosis, Salmonella infection, HIV infection, severe acute respiratory syndrome (SARS), and Japanese encephalitis.

[Method of Administration]

The mode of administration of the immunopotentiating agent of the present invention is not particularly limited, and may be either systemic or local administration. Specific examples of the mode of administration of the immunopotentiating agent of the present invention include oral administration, intraperitoneal administration, intravascular (intraarterial or intravenous) administration, transpulmonary administration, subcutaneous administration, and intramucosal administration. Note that intravascular administration is intended to include not only intravascular injection but also continuous infusion. Among these modes of administration, oral administration may be preferred.

The timing of administration of the immunopotentiating agent of the present invention may be selected as appropriate, depending on the use of the immunopotentiating agent, or the pathological condition of the subject to which the immunopotentiating agent is applied, for example. For example, when the immunopotentiating agent of the present invention is used for potentiating tumor immunity, the immunopotentiating agent of the present invention may be administered before, during, and/or after immunotherapy for a tumor-bearing patient. For example, when the immunopotentiating agent of the present invention is used for preventing an infection by potentiating infection immunity, the immunopotentiating agent of the present invention may be administered before, concurrently, and/or after the administration of a vaccine for an infection.

The dose of the immunopotentiating agent of the present invention may be determined as appropriate, depending on the use of the immunopotentiating agent, or the pathological condition or age of the subject to which the immunopotentiating agent is applied, for example, and cannot be uniquely determined. For example, the immunopotentiating agent of the present invention may be administered at a single dose of approximately 400 to 800 mg/body, calculated as the amount of imatinib and/or a salt thereof, at a frequency of once or twice/day.

[Dosage Forms]

While the dosage form of the immunopotentiating agent of the present invention is not particularly limited, and may be selected as appropriate, depending on the mode of administration or the like, examples thereof include tablets (including sugar-coated tablets and film-coated tablets), pills, granules, powders, capsules (including soft capsules), and liquids (including syrups, emulsions, and suspensions). These dosage forms can be prepared using pharmacologically acceptable bases or additives, and the types or amounts of the bases or additives to be incorporated are also known in the field of pharmaceutical technologies.

When the immunopotentiating agent of the present invention is used for potentiating tumor immunity, the immunopotentiating agent of the present invention may be formulated into a drug together with a drug used for immunotherapy. When the immunopotentiating agent of the present invention is used for potentiating infection immunity, the immunopotentiating agent of the present invention may be formulated into a drug together with a vaccine for an infection or a therapeutic drug for an infection.

2. Agent for Suppressing Regulatory T Cells

The present invention is an agent for suppressing Tregs used for reducing Tregs, which comprises imatinib and/or a salt thereof as an active ingredient.

The subject to which the suppressing agent of the present invention is applied is not particularly limited as long as the subject is in need of a reduction in Tregs. One suitable example may be a subject in need of potentiation of tumor immunity or infection immunity, as described for "1. Immunopotentiating Agent" above. The suppressing agent of the present invention can also effectively reduce effector Tregs, and thus, is suitably used as an agent for suppressing effector Tregs.

With regard to the suppressing agent of the present invention, the type of the active ingredient, the method of administration, the dosage form, and the like are the same as described for "1. Immunopotentiating Agent" above.

3. Testing Method for Predicting Therapeutic Efficacy in a Patient with Chronic Myelogenous Leukemia Receiving Administration of Imatinib and/or a Salt Thereof The present invention is a testing method for predicting therapeutic efficacy in a patient with chronic myelogenous leukemia receiving administration of imatinib and/or a salt thereof, the method comprising counting Tregs contained in peripheral blood collected from the patient with chronic myelogenous leukemia receiving administration of imatinib and/or a salt thereof, and predicting therapeutic efficacy of imatinib and/or a salt thereof for chronic myelogenous leukemia based on the number of the Tregs.

In the testing method of the present invention, Tregs contained in the peripheral blood may be used as a biomarker. In view of more accurately predicting the therapeutic efficacy for chronic myelogenous leukemia, the number of effector Tregs is preferably used as a biomarker. The "effector Tregs" herein denotes $CD45RA^-FOXP3^{high}CD4^+$ T cells, which have a typical Treg characteristic such as producing only small amounts of cytokines, and are distinguished from naive Tregs showing $CD45RA^-FOXP3^{low}CD4^+$. As used herein, the "$FOXP3^{high}$" denotes high expression of FOXP3, and refers to expression of FOXP3 at a level higher than the maximum FoxP3 expression level in CD4-positive, CD45RA-positive, and FoxP3-positive cells (naive Tregs) derived from peripheral blood mononuclear cells. As used herein, the "$FOXP3^{low}$" refers to expression of FOXP3 at a level comparable to the FoxP3 expression level in CD4-positive, CD45RA-positive, and FoxP3-positive cells (naive Tregs) derived from peripheral blood mononuclear cells.

In the testing method of the present invention, the number of Tregs in the peripheral blood can be measured by counting cells expressing CD4, CD45RA, and FoxP3 from human peripheral blood mononuclear cells contained in the peripheral blood. For the expression of CD4, CD45RA, and FoxP3, the cells may be labeled or separated using labeled antibodies or the like, and may be subjected to FACS analysis utilizing these markers, thereby measuring the number of Tregs in the peripheral blood.

In the testing method of the present invention, a patient with a reduction in the number of Tregs (in particular, effector Tregs) in the peripheral blood is determined as having high therapeutic efficacy of imatinib and/or a salt thereof for chronic myelogenous leukemia, and having the possibility that complete molecular response (CMR) may be achieved. The "reduction in the number of Tregs" herein can be confirmed as follows, for example: (1) the number of Tregs is found to be less than the number of Tregs in the peripheral blood before the administration of imatinib and/or a salt thereof; (2) the number of Tregs in peripheral blood is measured in advance for a patient who has achieved CMR and a Non-CMR patient in the treatment of chronic myelogenous leukemia with imatinib and/or a salt thereof, and the number of Tregs is found to be comparable to the number of Tregs in the peripheral blood derived from the patient who has achieved CMR; or (3) the number of Tregs in the peripheral blood of a healthy donor is measured in advance, and the number of Tregs is found to be less than the number of Tregs in the peripheral blood derived from the healthy donor.

On the other hand, in the testing method of the present invention, a patient without a reduction in the number of Tregs in the peripheral blood is estimated as having low therapeutic efficacy of imatinib and/or a salt thereof for chronic myelogenous leukemia, and having the possibility that CMR may not be achieved. These test results can be used when changing the therapeutic strategy, such as stopping the administration of imatinib and/or a salt thereof.

The present invention further provides a reagent for detecting Tregs contained in peripheral blood, as a testing kit for performing the above-described testing method. Examples of the reagent for detecting Tregs include, but are not particularly limited to, antibodies such as anti-CD4 antibody, anti-CD45RA antibody, and anti-FoxP3 antibody. In the testing kit, these antibodies may be labeled with biotin, fluorescent labels, magnetic beads, and the like, as required.

EXAMPLES

The present invention will be specifically described hereinafter, with reference to examples; however, the present invention is in no way limited to these examples.

Test Example 1

For patients with chronic myelogenous leukemia (87 patients; CMR patients: 49; and Non-CMR patients: 38) treated by administration of Gleevec (Novartis Pharma K.K.; active ingredient: imatinib mesylate), the proportion of Tregs in the peripheral blood collected after the treatment was measured. Specifically, peripheral blood mononuclear cells in the peripheral blood were harvested, $CD4^+$ cells were gated using anti-CD4 antibody labeled with BD Horizon V500, and the cells were stained with FITC-labeled anti-CD45RA antibody and PE-labeled anti-FoxP3 antibody. Subsequently, CD45RA and FoxP3 expression levels were measured by FACS analysis. For comparison, the proportion of Tregs in the peripheral blood of a healthy donor was similarly measured.

Figure 2:
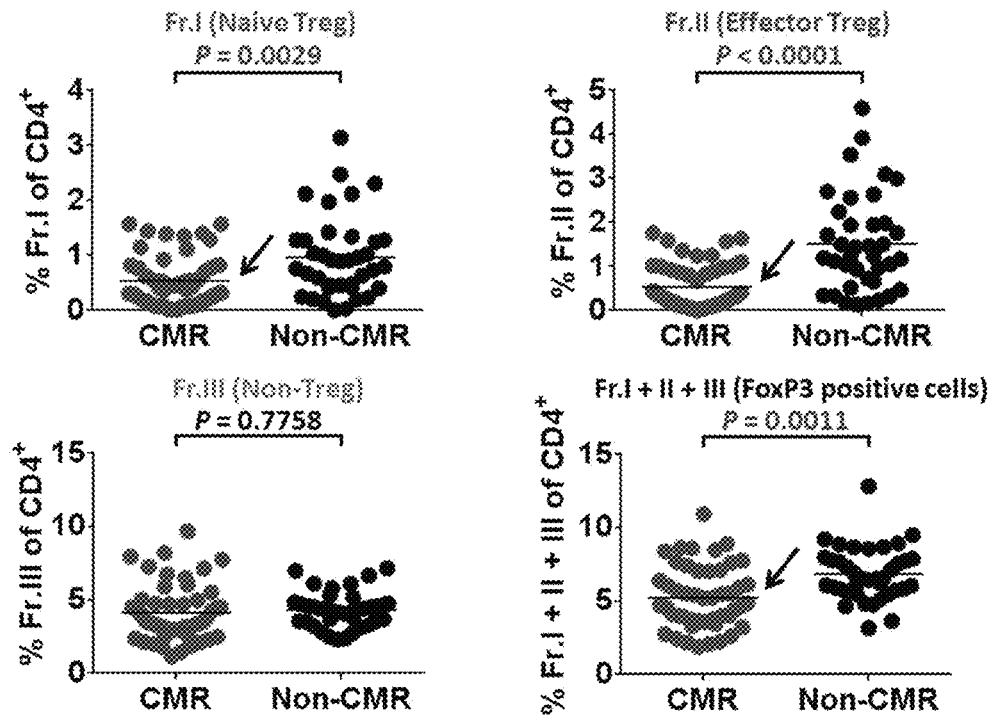
FIG. 2 shows the results of measurement of the proportions of naive Tregs (fraction I in FIG. 1), effector Tregs (fraction II in FIG. 1), Non-Tregs (fraction III in FIG. 1), and FoxP3-positive cells (fraction I+II+III in FIG. 1) contained in CD4-positive cells in the peripheral blood of 87 patients (CMR patients: 49; Non-CMR patients: 38) examined in Test Example 1.

The results are shown in FIGS. 1 and 2. FIG. 1 shows the results of measurement of CD45RA and FoxP3 expression levels for CD4-positive cells derived from the peripheral blood of two CMR patients, two Non-CMR patients, and one healthy donor. In FIG. 1, fraction I ($CD45RA^+ FoxP3^{low}$) represents naive Tregs, fraction II ($CD45RA^- FoxP3^{high}$) represents effector Tregs, and fraction III ($CD45RA^-FoxP3^{low}$) represents non-suppressive Tregs. FIG. 2 shows the results of measurement of the proportions of naive Tregs (fraction I in FIG. 1), effector Tregs (fraction II in FIG. 1), Non-Tregs (fraction III in FIG. 1), and $FoxP3^+$ (fraction I+II+III in FIG. 1) contained in $CD4^+$ cells in the peripheral blood of the 87 patients (CMR patients: 49; Non-CMR patients: 38).

As is clear from FIGS. 1 and 2, the CMR patients showed a significant reduction in the proportion of effector Tregs (fraction II in FIG. 1), whereas the Non-CMR patients showed no reduction in the proportion of effector Tregs. Similarly, the CMR patients showed a reduction in naive Tregs, whereas the Non-CMR patients showed no reduction in naive Tregs.

The foregoing results revealed that the number of Tregs (in particular, the number of effector Tregs) is reduced in CMR patients, and thus, the therapeutic efficacy of the administration of imatinib mesylate in patients with chronic myelogenous leukemia can be estimated by measuring the number of Tregs. The results also indicate that the therapeutic efficacy of imatinib mesylate in patients with chronic myelogenous leukemia is dependent on the reduction in the number of Tregs.

Test Example 2

Because the reduction in Tregs, in particular, the reduction in effector Tregs, was observed in the CMR patients, the effects of the reduction in Tregs upon CD8+ killer T cells were examined in this test. Specifically, for the same patients with chronic myelogenous leukemia (87 patients; CMR patients: 49; and Non-CMR patients: 38) as those tested in Test Example 1 above, the state of CD8+ T cells in the peripheral blood collected after the treatment was measured. Specifically, peripheral blood mononuclear cells in the peripheral blood were harvested, CD8+ T cells were gated using PE-Cy7 anti-CD8 antibody, and the cells were stained with PerCP-Cy5.5-labeled anti-CCR7 antibody and FITC-labeled anti-CD45RA antibody. Subsequently, CCR7 and CD45RA expression levels were measured by FACS analysis. For comparison, the state of CD8+ T cells in the peripheral blood of a healthy donor was similarly measured.

Figure 3:
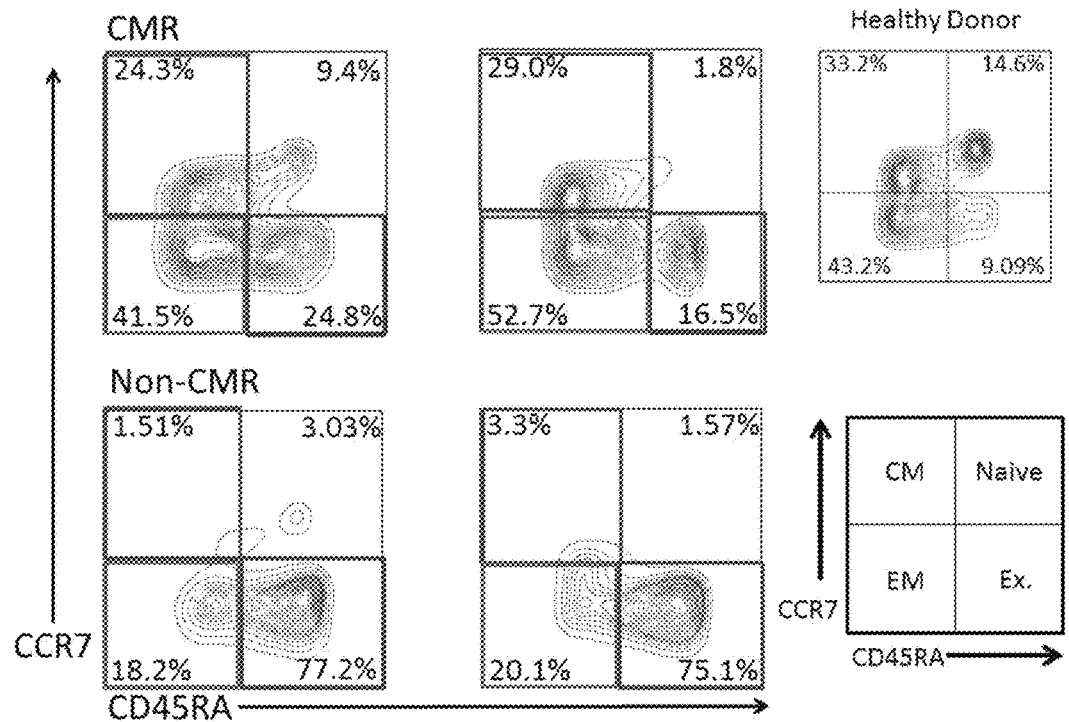
FIG. 3 shows the results of measurement of CCR7 and CD45RA expression levels for CD8-positive T cells derived from the peripheral blood of representative two CMR patients, two Non-CMR patients, and one healthy donor in Test Example 2.
Figure 4:
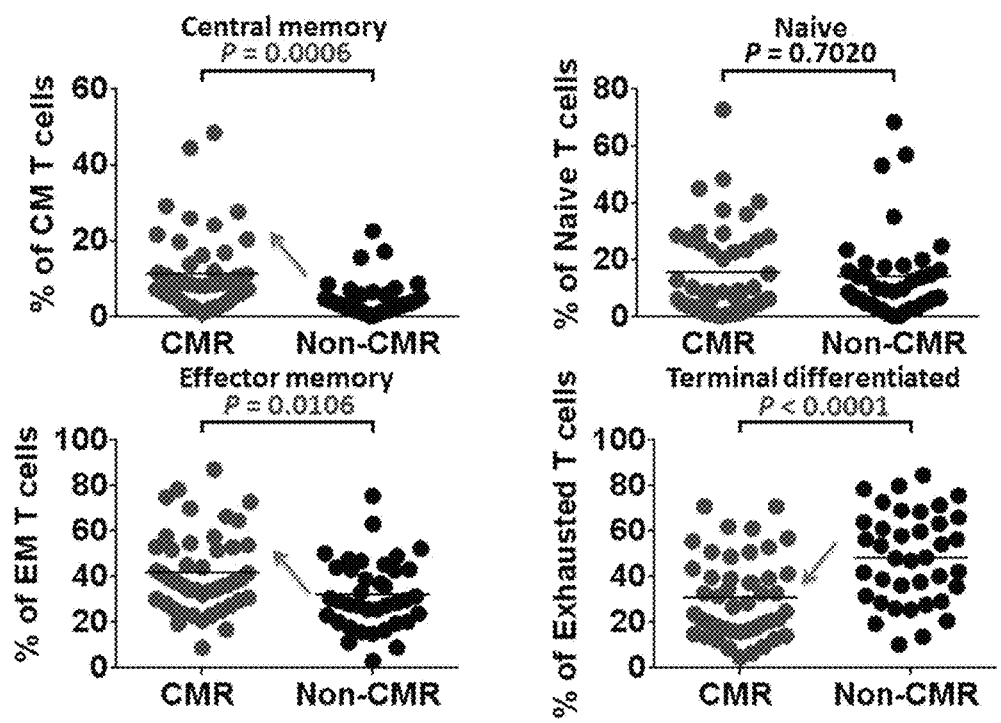
FIG. 4 shows the results of measurement of the proportions of central memory T cells, effector memory T cells, naive T cells, and exhausted T cells contained in CD8-positive T cells in the peripheral blood of 87 patients (CMR patients: 49; Non-CMR patients: 38) examined in Test Example 2.

The results are shown in FIGS. 3 and 4. FIG. 3 shows the results of measurement of CCR7 and CD45RA expression levels for CD8+ T cells derived from the peripheral blood of two CMR patients, two Non-CMR patients, and one healthy donor. In FIG. 3, the fraction of CCR7+CD45RA+ represents naive T cells (Naive), the fraction of CCR7+CD45RA− represents central memory T cells (CM), the fraction of CCR7−CD45RA+ represents exhausted T cells (Ex.), and the fraction of CCR7−CD45RA− represents effector memory T cells (EM). FIG. 4 shows the proportions of central memory T cells, effector memory T cells, naive T cells, and exhausted T cells relative to the CD8-positive T cells in the peripheral blood of the 87 patients (CMR patients: 49; Non-CMR patients: 38).

As is clear from FIGS. 3 and 4, the CMR patents showed a reduction in exhausted T cells (CCR7−CD45RA+) compared to the Non-CMR patients, indicating the activation of tumor immunity responses elicited by the reduction in effector Tregs.

Test Example 3

CD4+ cells were harvested from the peripheral blood collected from a healthy donor, using APC-Cy7 anti-CD4 antibody. From the harvested CD4+ cells, CD45RA+FoxP3$^{low}$ cells (fraction I: naive Tregs), CD45RA−FoxP3$^{high}$ cells (fraction II: effector Tregs), and CD45RA+FoxP3− cells (fraction V) were fractionated using FITC anti-CD45RA antibody and PE-labeled anti-FoxP3 antibody. Native CD8+ T cells were also fractionated using BD Horizon V500 anti-CD8 antibody, PerCP-Cy5.5-labeled anti-CCR7 antibody, and BD Horizon V450-labeled anti-CD45RA antibody from the peripheral blood collected from the healthy donor. Cells of each fraction were seeded at 20,000 cells/200 μl onto RPMI1640 medium, Gleevec (Novartis Pharma K.K.; active ingredient: imatinib mesylate) was added to give the amounts of imatinib shown in FIG. 5, and the cells were cultured at 37° C. for 5 days. After the culture, viable cells were stained with a Fixable Viability Dye.

Figure 5:
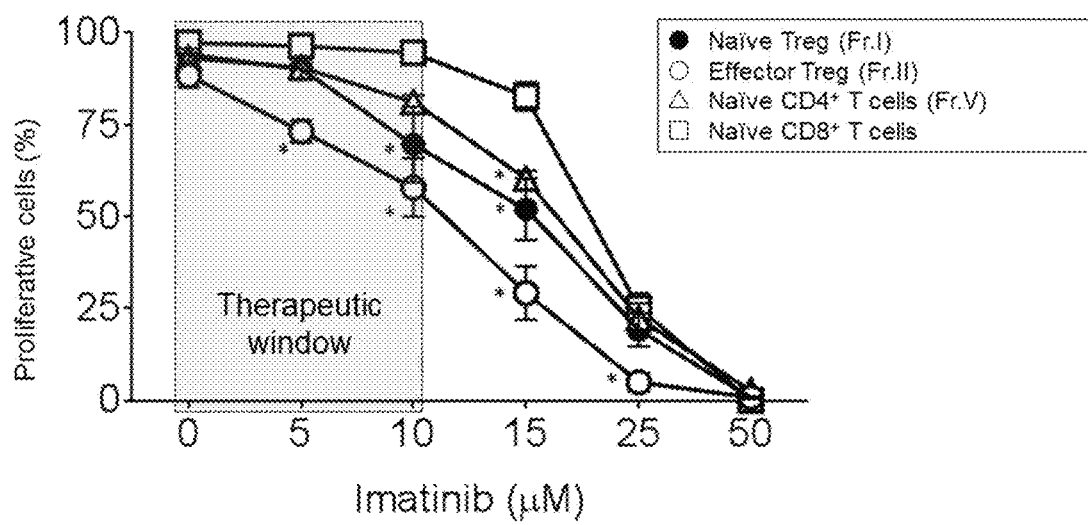
FIG. 5 shows the results of measurement of proliferative capacity after the addition of imatinib for CD4-positive cells and naive $CD8^+$ T cells derived from the peripheral blood of a healthy donor in Test Example 3.

The results are shown in FIG. 5. FIG. 5 shows the results obtained by calculating, for each of the fractions of CD4-positive cells, the proportion of cells that underwent cell division (proliferation) twice or more, based on the degree of reduction in staining intensity of fluorescent dye CFSE (CFSE dilution) for the cells of each fraction. These results revealed that the addition of imatinib significantly suppresses the proliferation of effector Tregs (CD45RA−FoxP3$^{high}$: fraction II).

Test Example 4

CD45RA+FoxP3$^{low}$ cells (fraction I: naive Tregs), CD45RA−FoxP3$^{high}$ cells (fraction II: effector Tregs), CD45RA+FoxP3− cells (fraction V), and naive CD8+ T cells were fractionated from the peripheral blood of a healthy donor, as in Test Example 3 above. Cells of each fraction were seeded at 20,000 cells/200 μl onto RPMI1640 medium, Gleevec (Novartis Pharma K.K.; active ingredient: imatinib mesylate) was added to give the amounts of imatinib shown in FIG. 6, and the cells were cultured at 37° C. for 5 days. After the culture, apoptosis was measured by staining with Annexin V and 7-AAD.

Figure 6:
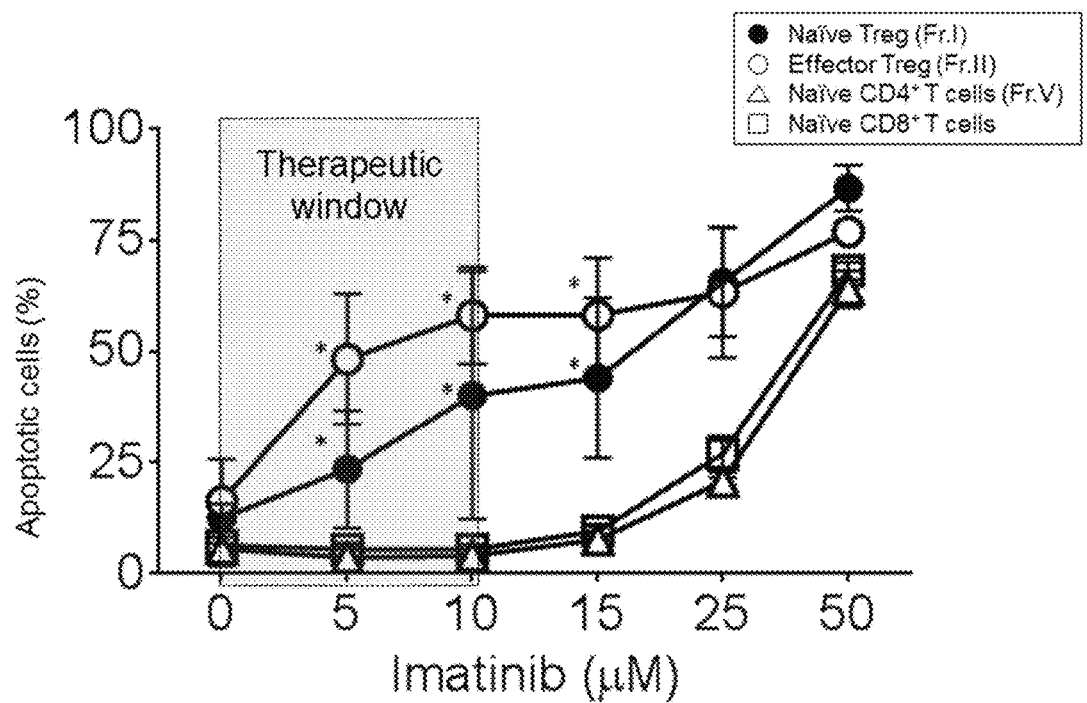
FIG. 6 shows the results of measurement of apoptosis induction after the addition of imatinib for CD4-positive cells and naive $CD8^+$ T cells derived from the peripheral blood of a healthy donor in Test Example 4.

The results are shown in FIG. 6. FIG. 6 shows a graph plotting the proportion of apoptotic cells during the culture. In support of the results of Test Example 3, these results confirmed that the addition of imatinib increases the proportion of apoptotic cells for CD45RA−FoxP3$^{high}$ cells (fraction II: effector Tregs).

Test Example 5

In order to deny the possibility that the reduction in effector Tregs was caused by the achievement of CMR in the patients with chronic myelogenous leukemia treated by the administration of Gleevec, the proportion of Tregs was examined in three patients (Cases 1, 2 and 3) in which CMR was not achieved by the administration of Gleevec, but was achieved after switching to the administration of nilotinib in the course of treatment. Specifically, the proportion of effector Tregs in the peripheral blood when CMR was not achieved after the administration of Gleevec and the proportion of effector Tregs in the peripheral blood when CMR was achieved after switching to the administration of nilotinib were measured as in Test Example 1 above.

Figure 7:
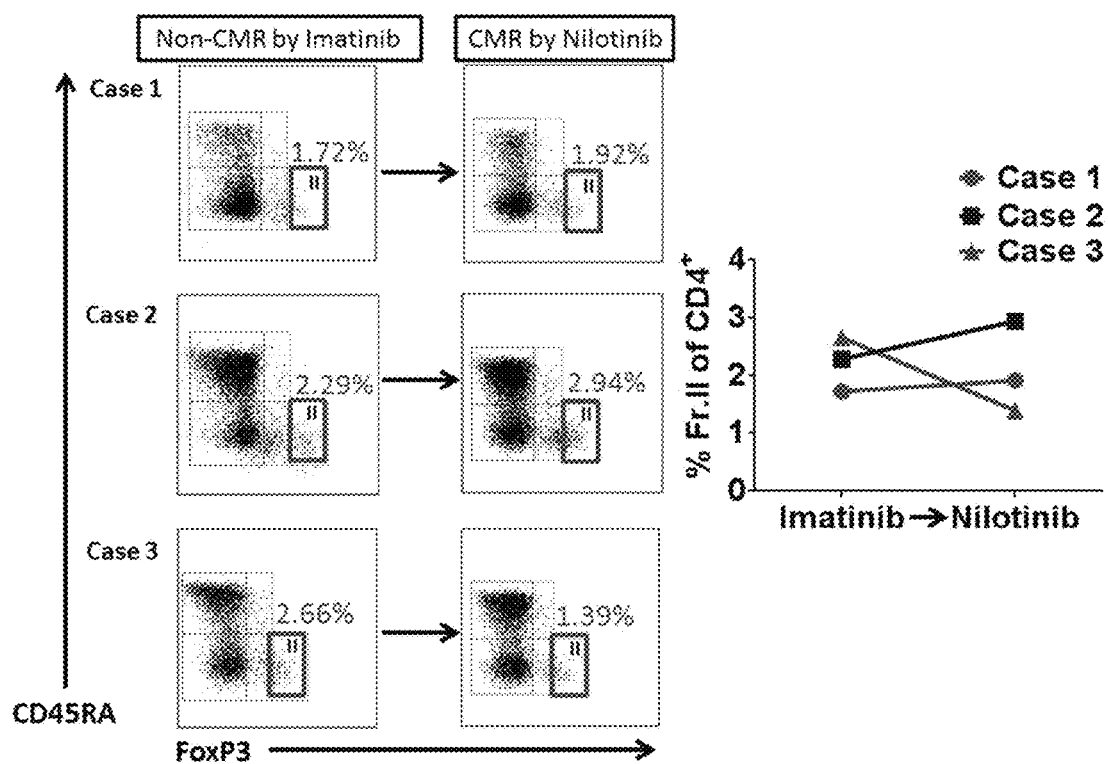
FIG. 7 shows the results obtained for three patients (Cases 1, 2 and 3) in which CMR was not achieved by the administration of Gleevec (imatinib), but was achieved after switching to the administration of nilotinib in the course of treatment, by measuring the proportion of Tregs in the peripheral blood in the Non-CMR state after the administration of Gleevec, and the proportion of Tregs in the peripheral blood in the CMR state after the administration of nilotinib in Test Example 5.

The results are shown in FIG. 7. As is clear from FIG. 7, although CMR was achieved by the administration of nilotinib, a reduction in effector Tregs was not observed. Furthermore, given that nilotinib has higher affinity for BCR-ABL than that of imatinib, the effector Treg-reducing action of imatinib was believed to be produced using a kinase other than BCR-ABL as the target.

Test Example 6

The activation of cancer antigen-specific immune responses, elicited by a reduction in effector Tregs caused by the administration of imatinib, was investigated in vitro. Initially, Gleevec (Novartis Pharma K.K.; active ingredient: imatinib mesylate) was added at an imatinib concentration of 5 μM into peripheral blood derived from three healthy donors (HD1, HD2 and HD3) and cultured at 37° C. for 1 day. Subsequently, cancer antigen (Melan-A) was added at a concentration of 10 μM to stimulate the cells, and the cells were cultured at 37° C. for 10 days. After the culture, the number of effector Tregs was measured as in Test Example 1 above. In addition, after the culture, specific CD8+ T cells were analyzed using BD Horizon V500-labeled anti-CD8 antibody and PE-labeled Melan A/HLA-A*0201 tetramer to examine Melan A-specific CD8+ T cell induction. In the case of the healthy donor-derived peripheral blood (HD1), instead of cancer antigen (Melan-A) described above, cytomegalovirus antigen was added at a concentration of 10 μM to stimulate the cells, and the cells were cultured under the same conditions as described above. Analysis on specific CD8+ T cell induction was then performed as with Melan A, using BD Horizon V500-labeled anti-CD8 antibody and PE-labeled CMV/HLA-A*0201 tetramer.

Figure 8:
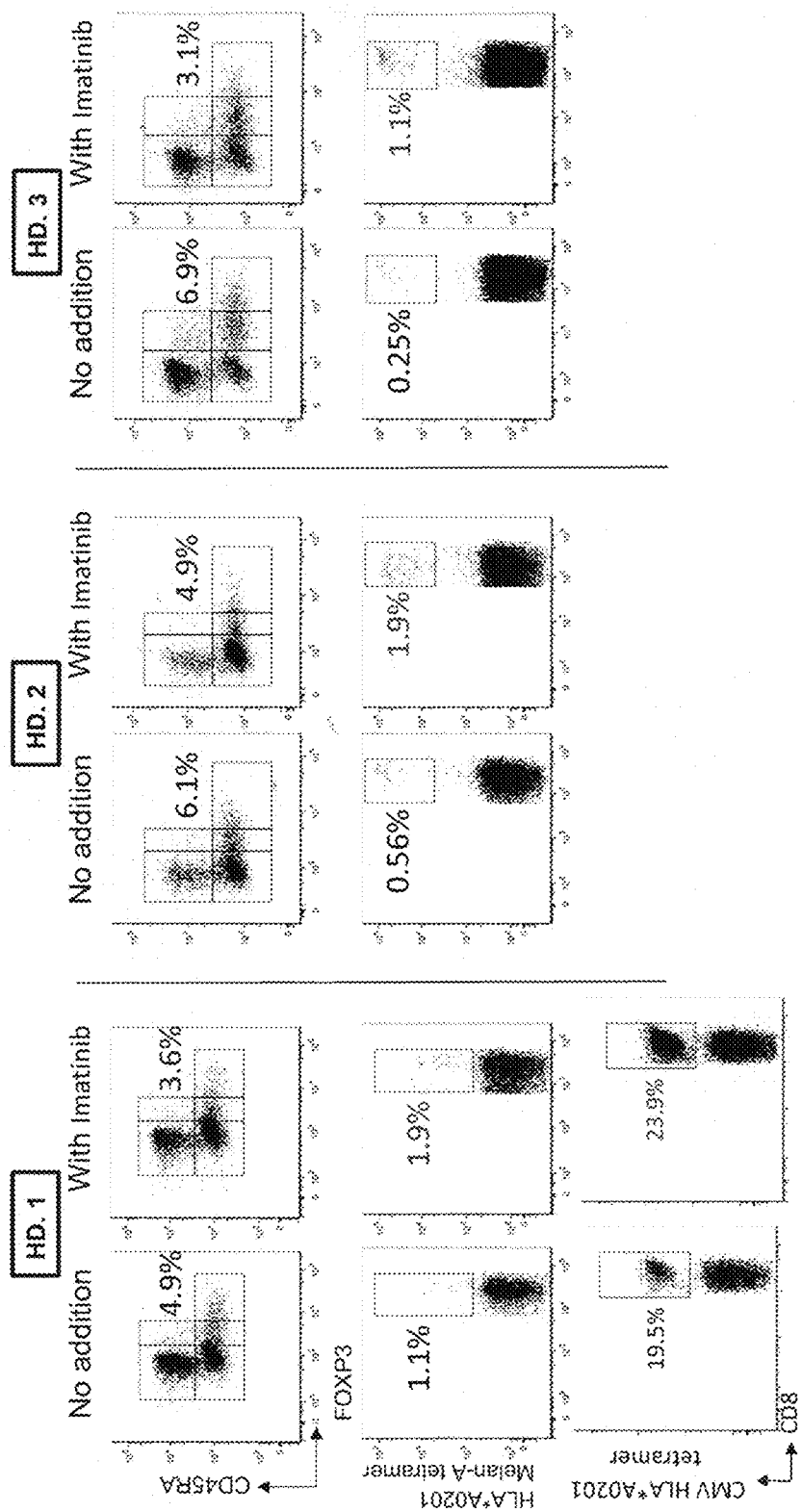
FIG. 8 shows the results of measurement of the proportion of effector Tregs and the proportion of antigen-specific $CD8^+$ T cells, after the addition of imatinib into peripheral blood derived from three healthy donors (HD1, HD2 and HD3), and further addition of cancer antigen (Melan-A) or cytomegalovirus antigen to stimulate the cells in Test Example 6.

The results are shown in FIG. 8. These results confirmed that the addition of imatinib induces a reduction in effector Tregs, which, in turn, leads to the potentiation of Melan-A- specific CD8⁺ T cell induction. Similarly, the addition of imatinib and stimulation with cytomegalovirus antigen potentiated the induction of cytomegalovirus-specific CD8⁺ T cells.

Test Example 7

The activation of immune responses against malignant melanoma, elicited by a reduction in effector Tregs caused by the administration of imatinib, was investigated in vitro. Initially, Gleevec (Novartis Pharma K.K.; active ingredient: imatinib mesylate) was added at an imatinib concentration of 5 µM into peripheral blood derived from three patients with malignant melanoma (Pt 1, Pt2 and Pt3) and cultured at 37° C. for 1 day. Subsequently, cancer antigen (Melan-A) was added at a concentration of 10 µM to stimulate the cells, and the cells were cultured at 37° C. for 10 days. After the culture, the number of effector Tregs was measured as in Test Example 1 above. In addition, after the culture, analysis with the tetramer was performed as in Test Example 6 above to examine specific CD8⁺ T cell induction.

Figure 9:
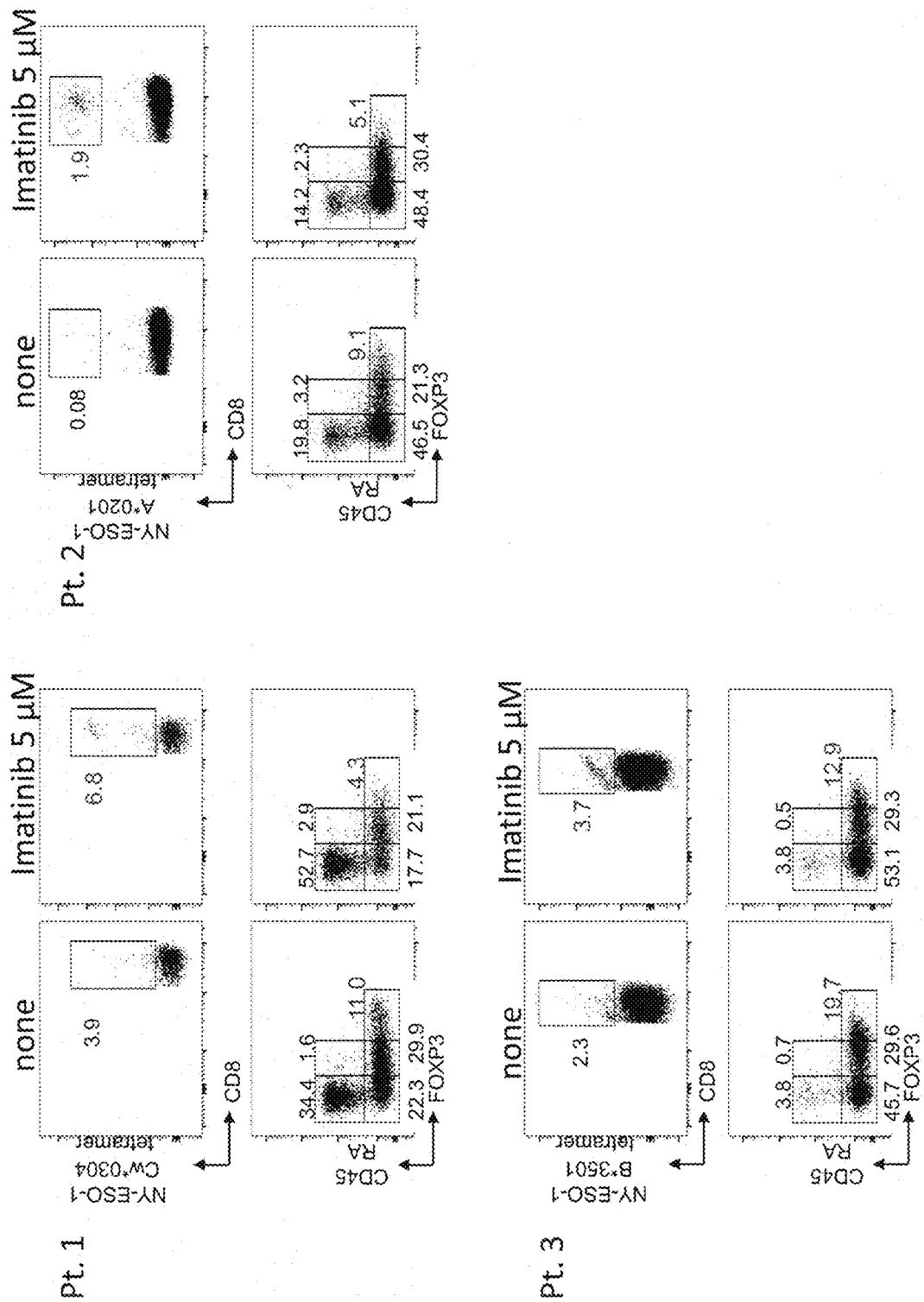
FIG. 9 shows the results of measurement of the proportion of effector Tregs and the proportion of antigen-specific $CD8^+$ T cells, after the addition of imatinib into peripheral blood derived from three patients with malignant melanoma (Pt1, Pt2 and Pt3), and further addition of cancer antigen (Melan-A) to stimulate the cells in Test Example 7.

The results are shown in FIG. 9. These results also revealed that the administration of imatinib induces a reduction in effector Tregs in the peripheral blood of patients with malignant melanoma, which leads to the activation of immune responses against malignant melanoma.

Test Example 8

The activation of infection immune responses, elicited by a reduction in effector Tregs caused by the administration of imatinib, was investigated in vitro. Specifically, analysis on specific CD8⁺ T cell induction was performed as in Test Example 6 above, except that instead of cytomegalovirus antigen, an influenza virus antigen peptide was added at a concentration of 10 µM to stimulate the cells, and that influenza-specific tetramer was used.

Figure 10:
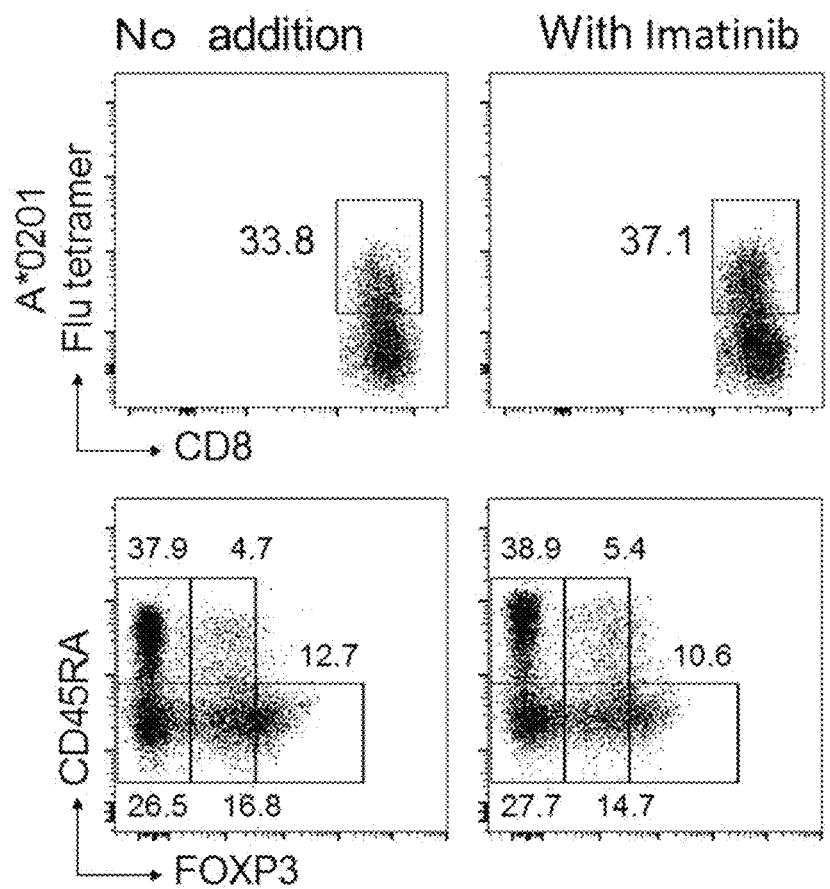
FIG. 10 shows the results of measurement of the proportion of effector Tregs and the proportion of antigen-specific CD8$^+$ T cells, after the addition of imatinib into peripheral blood derived from a healthy donor, and further addition of an influenza virus antigen to stimulate the cells in Test Example 8.

The results are shown in FIG. 10. These results confirmed that the addition of imatinib and stimulation with influenza virus antigen potentiates the induction of influenza virus-specific CD8⁺ T cells.

Test Example 9

The following test was performed to examine the target molecule of imatinib in inducing a reduction in Tregs. Initially, CD45RA⁻FoxP3$^{high}$ cells (fraction II: effector Tregs), CD45RA⁺FoxP3⁻ cells (fraction V), and naive CD8⁺ T cells were fractionated from the peripheral blood of a healthy donor, as in Test Example 3 above. Cells of each fraction were seeded at 20,000 cells/200 µl onto RPMI1640 medium, Gleevec (Novartis Pharma K.K.; active ingredient: imatinib mesylate) was added at an imatinib concentration of 0 µM or 10 µM, and the cells were cultured at 37° C. for 1 hour. After the culture, cells of each fraction were harvested and treated with NP-40 lysis buffer to obtain cell lysates. The cell lysates were then subjected to Western blotting, using anti-lymphocyte-specific protein tyrosine kinase (LCK) antibody (3A5) and anti-phosphorylated Src Family (phopsho-Src Family) antibody (polyclonal antibody) as primary antibodies, and further using HRP-labeled antibody as a secondary antibody.

Figure 11:
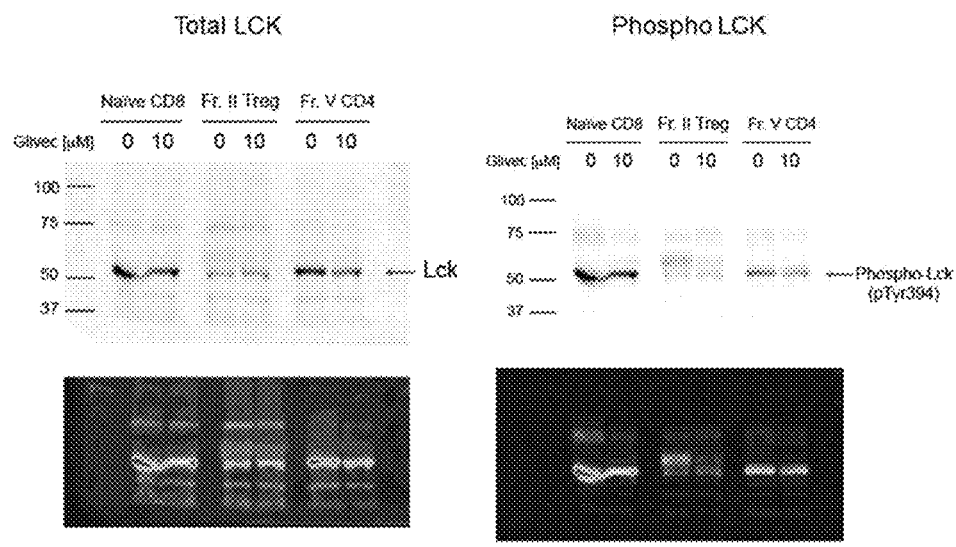
FIG. 11 shows the results of Western blot measurement of the effects of imatinib upon the expression levels of lymphocyte-specific protein tyrosine kinase (LCK) and phosphorylated LCK, for naive CD8$^+$ T cells, effector Tregs (Fr. II Tregs), and CD45RA$^+$FoxP3$^-$ cells (Fr. V CD4) derived from the peripheral blood of a healthy donor in Test Example 9.

The results are shown in FIG. 11. These results showed that in naive CD8⁺ T cells and CD45RA⁺FoxP3⁻ cells (fraction V), LCK was expressed without the addition of imatinib, and phosphorylated LCK was sufficiently expressed with the addition of imatinib, although its expression level decreased. On the contrary, in effector Tregs, a low level of LCK was expressed without the addition of imatinib, and phosphorylated LCK was scarcely expressed with the addition of imatinib. The foregoing results indicated the possibility that imatinib induced a reduction in Tregs, using LCK as the target molecule.

Test Example 10

With regard to LCK indicated as being a possible target molecule of imatinib in inducing a reduction in Tregs, the expression of LCK in CD4⁺ T cells and CD8⁺ T cells was investigated. The expression levels of target molecules (ABL1, ABL2, KIT, PDGFRA, LCK, NQO2, and DDR1) having high affinity for imatinib were analyzed, using gene transcription initiation site database (FANTOM5 deep CAGE database) prepared using CD4-positive T cells and CD8-positive T cells in the peripheral blood collected from healthy donors. Data of CNhs 13223 and CNhs 12201 from the HeliScope CAGE libraries were used in the analysis, and tag counts of transcription initiation sites (TSS tag counts) were plotted as graphs.

Figure 12:
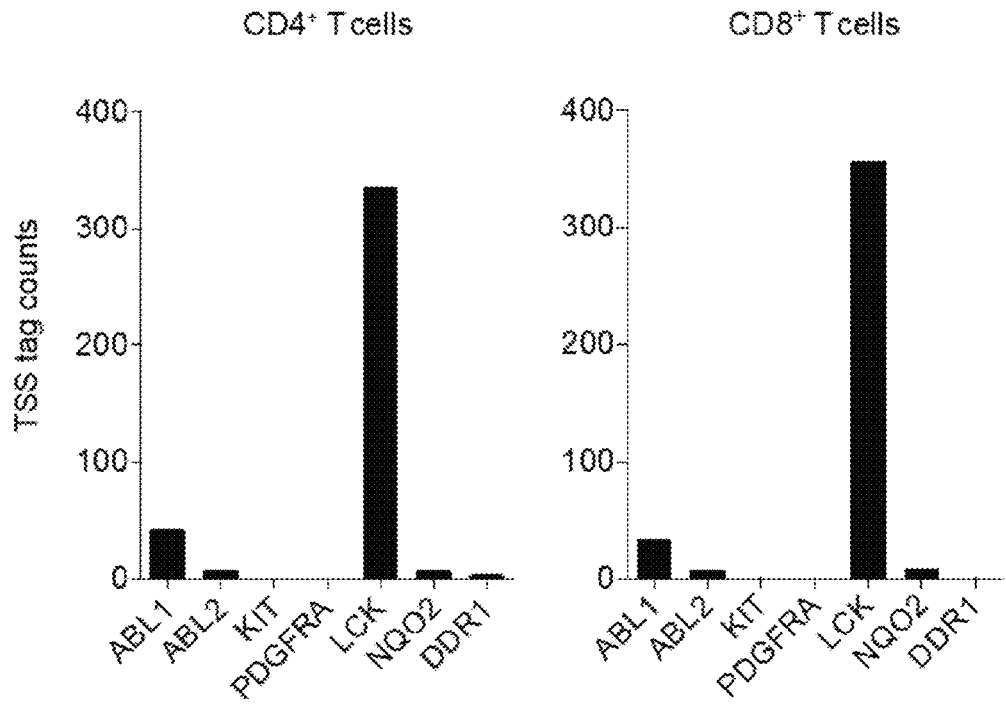
FIG. 12 shows the results of analysis of the expression levels of target molecules (ABL1, ABL2, KIT, PDGFRA, LCK, NQO2, and DDR1) having high affinity for imatinib in CD4$^+$ T cells and CD8$^+$ T cells derived from the peripheral blood of a healthy donor in Test Example 10.

The results are shown in FIG. 12. These results revealed that CD4⁺ T cells and CD8⁺ T cells both expressed high levels of LCK.

Test Example 11

The expression levels of LCK and its downstream molecule ZAP-70 in T cells were investigated. Initially, CD4⁺ T cells and CD8⁺ T cells were isolated from the peripheral blood collected from a healthy donor, using APC anti-CD4 antibody and BD Horizon V500 anti-CD8 antibody. In addition, CD45RA⁺FoxP3$^{low}$ cells (fraction I: naive Tregs) and CD45RA⁻FoxP3$^{high}$ cells (fraction II: effector Tregs) were isolated from the peripheral blood collected from the healthy donor, as in Test Example 3 above. The expression levels of LCK and ZAP-70 mRNAs in cells of each of the fractions were investigated using qRT-PCR. As a control, GAPDH mRNA was used in the analysis of the expression levels of LCK and ZAP-70 mRNAs.

Figure 13:
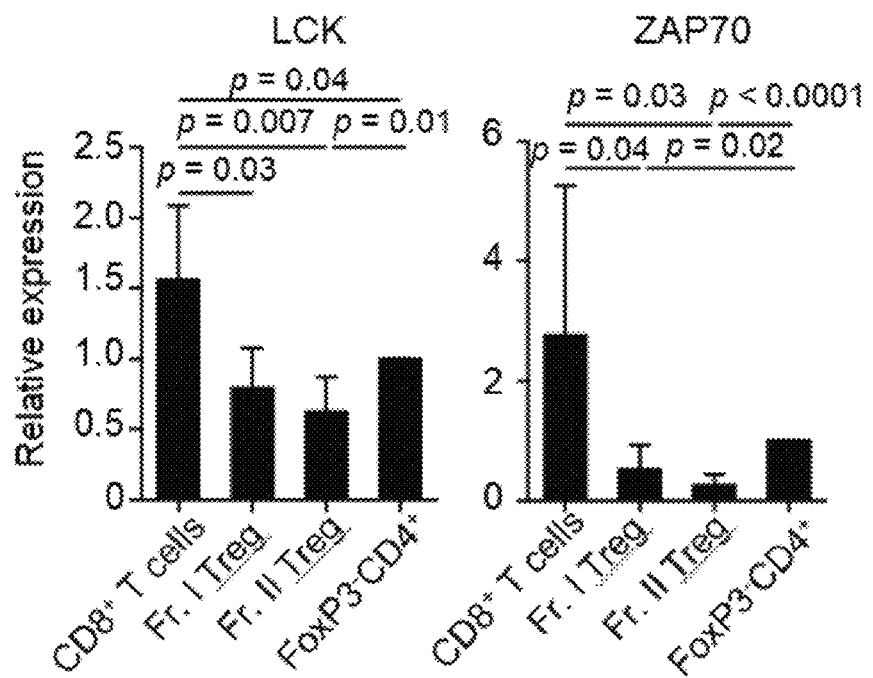
FIG. 13 shows the results of analysis of the expression levels of LCK and ZAP-70 mRNAs for CD8$^+$ T cells, CD4$^+$ T cells, CD45RA$^+$FoxP3$^{low}$ cells (fraction I: naive Tregs), and CD45RA$^-$FoxP3$^{high}$ cells (fraction II: effector Tregs) derived from the peripheral blood of a healthy donor in Test Example 11.

The results are shown in FIG. 13. These results revealed that CD4⁺ T cells and CD8⁺ T cells both expressed high levels of LCK. It was revealed that the expression levels of LCK, which plays an important role as a T cell receptor signaling molecule, and its downstream molecule ZAP-70, were lower in CD45RA⁺FoxP3$^{low}$ cells (fraction I: naive Tregs) and CD45RA⁻FoxP3$^{high}$ cells (fraction II: effector Tregs) than in CD8⁺ T cells.

Test Example 12

Foxp3-bound regions in human Treg cells were analyzed from the SRA (Sequence Read Archive) database, and were mapped to LCK gene and ZAP-70 gene. In the analysis, SRX060160 data from SRA was used.

Figure 14:
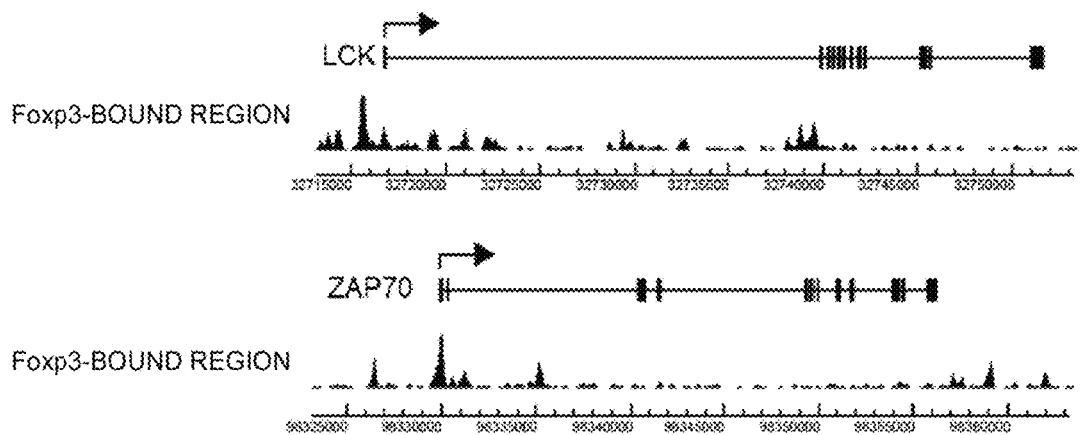
FIG. 14 shows the results of analysis obtained by analyzing Foxp3-bound regions in human Treg cells from the SRA (Sequence Read Archive) database, and mapping them to LCK gene and ZAP-70 gene in Test Example 12.

The results are shown in FIG. 14. In FIG. 14, an arrow represents the transcription initiation site of the gene, a rectangle represents each exon, and a waveform represents a Foxp3-bound region. The results showed that the Treg-specific Foxp3 transcription factor is bound to the promoter regions of LCK and ZAP-70 genes. That is, these results indicate that LCK and ZAP-70 are controlled in a Treg-specific manner.

Test Example 13

The expression levels of LCK and phospho-LckY394 in T cells, as well as the expression levels of LCK and phospho-LckY394 in T cells cultured in the presence of imatinib, were investigated. Initially, CD8$^+$ T cells were isolated from the peripheral blood collected from a healthy donor, using BD Horizon V500 anti-CD8 antibody. In addition, CD4$^+$ cells were harvested from the peripheral blood collected from the healthy donor, using APC-Cy7 anti-CD4 antibody. From the harvested CD4$^+$ cells, CD45RA$^+$FoxP3$^{low}$ cells (fraction I: naive Tregs), CD45RA$^-$FoxP3$^{high}$ cells (fraction II: effector Tregs), and FoxP3$^-$CD4$^+$ T cells were fractionated using FITC anti-CD45RA antibody and PE-labeled anti-FoxP3 antibody. T cells of each of the fractions were cultured for 1 hour in RPMI1640 medium containing 0 μM or 10 μM of imatinib (Gleevec; Novartis Pharma K.K.; active ingredient: imatinib mesylate). After the culture, T cells of each fraction were treated with NP-40 lysis buffer, and were subsequently subjected to Western blotting to measure the expression levels of LCK and phospho-LckY394. For the detection of LCK and phospho-LckY394, anti-Lck antibody (3A5) and anti-phosphorylated Src Family antibody (polyclonal) were used and colored with HRP-labeled secondary antibody.

Figure 15:
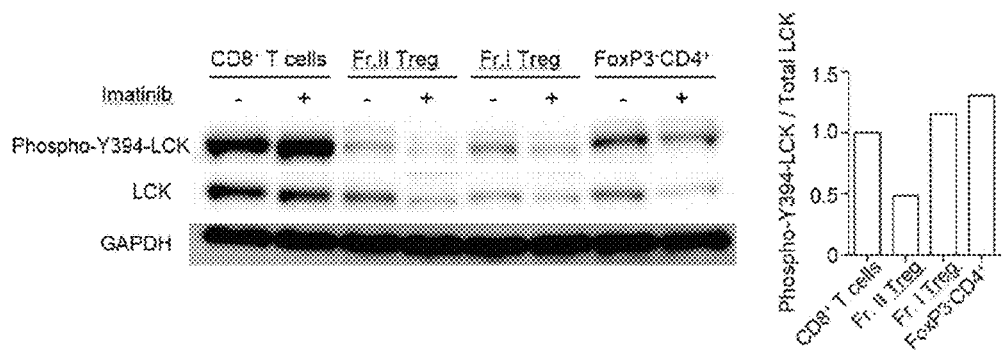
FIG. 15 shows the results of measurement of the expression levels of LCK and phospho-LckY394 in CD8$^+$ T cells, CD45RA$^+$FoxP3$^{low}$ cells (fraction I: naive Tregs), CD45RA$^-$FoxP3 cells (fraction II: effector Tregs), and FoxP3$^-$CD4$^+$ cells derived from the peripheral blood of a healthy donor in Test Example 13, wherein the graph at the right shows the ratio of band intensity measured by Western blotting.

The results are shown in FIG. 15. The results showed that the expression level of LCK protein was lower in CD45RA$^+$FoxP3$^{low}$ cells (fraction I: naive Tregs) and CD45RA$^-$FoxP3$^{high}$ cells (fraction II: effector Tregs) than in FoxP3$^-$CD8$^+$ T cells, and the phosphorylation level of LCK Y394 indicating the activity level of LCK was also low. It was also shown that when the cells were cultured with the addition of imatinib, the level of LCK protein and the phosphorylation level of LCK Y394 further decreased in CD45RA$^+$FoxP3$^{low}$ cells (fraction I: naive Tregs) and CD45RA$^-$FoxP3$^{high}$ cells (fraction II: effector Tregs).

Test Example 14

The inhibitory action of imatinib upon Treg cells was investigated in vivo. Specifically, BALB/c mice (8-week-old, female) were raised for 1 week during which they were orally or intraperitoneally administered once a day physiological saline containing Gleevec (Novartis Pharma K.K.; active ingredient: imatinib mesylate) in an amount of 0 mg, 2 mg, or 8 mg calculated as imatinib. One week after the start of the administration of imatinib, spleen cells were extracted from the mice and subjected to FACS analysis. The expression of Foxp3 and CD25 in CD4$^+$ T cells and the expression of Ki-67 and CD44 in CD4$^+$Foxp3$^+$ T cells were analyzed by FACS.

Figure 16:
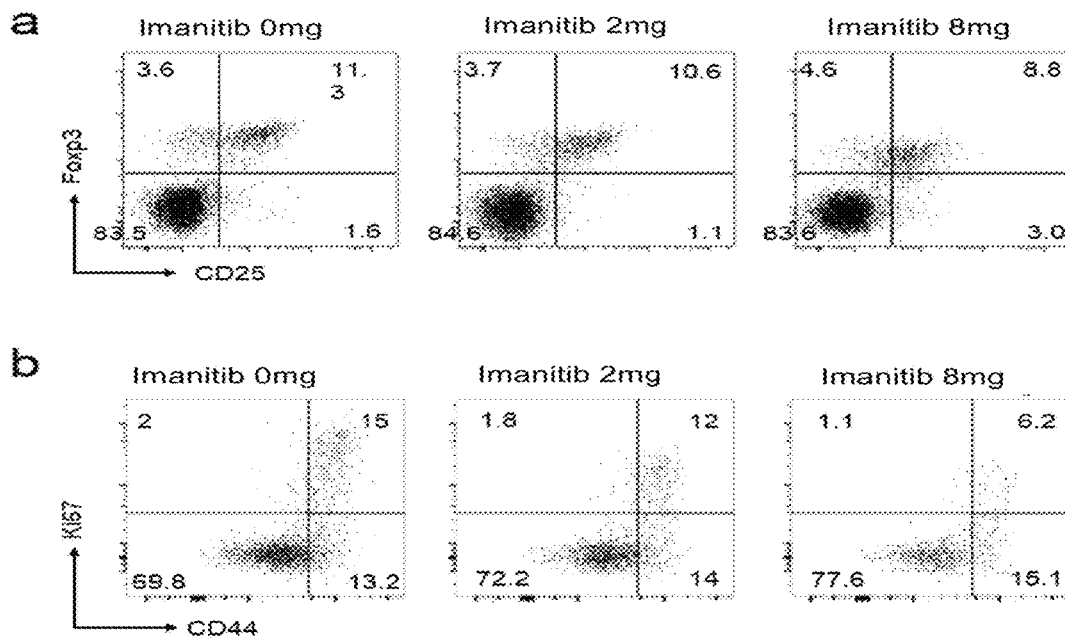
FIG. 16 shows the results of analysis of T cell surface markers for spleen cells extracted after the administration of 0 mg, 2 mg, or 8 mg of imatinib at a frequency of once a day for 1 week into BALB/c mice in Test Example 14, wherein "a" shows the results of measurement of the expression of Foxp3 and CD25 in CD4$^+$ T cells, and "b" shows the results of measurement of the expression of Ki-67 and CD44 in Foxp3$^+$ cells in "a".

The results are shown in FIG. 16. In FIG. 16, "a" shows the results of measurement of the expression of Foxp3 and CD25 in CD4$^+$ T cells, and "b" shows the results of measurement of the expression of Ki-67 and CD44 in CD4$^+$Foxp3$^+$ T cells in "a". These results confirmed that the administration of imatinib selectively inhibits Ki-67$^+$ Treg cells known to be highly proliferative.

Test Example 15

The expression level of Ki-67 in T cells and the expression level of Ki-67 in effector Treg cells cultured in the presence of imatinib were investigated. Initially, CD8$^+$ T cells, CD45RA$^+$FoxP3$^{low}$ cells (fraction I: naive Tregs), CD45RA$^-$FoxP3$^{high}$ cells (fraction II: effector Tregs), and FoxP3$^-$CD4$^+$ cells were fractionated from the peripheral blood collected from a healthy donor, as in Test Example 13. For cells of each of the fractions, the expression level of Ki-67 was measured by FACS analysis. In addition, CD45RA$^-$FoxP3$^{high}$ cells (fraction II: effector Tregs) were cultured for 4 days in RPMI1640 medium containing 10 μM of imatinib (Gleevec; Novartis Pharma K.K.; active ingredient: imatinib mesylate), and subsequently, the expression level of Ki-67 in the cultured cells was measured by FACS analysis. As a control, the same test as described above was performed, except that the medium not containing imatinib was used, and the expression level of Ki-67 was measured.

Figure 17:
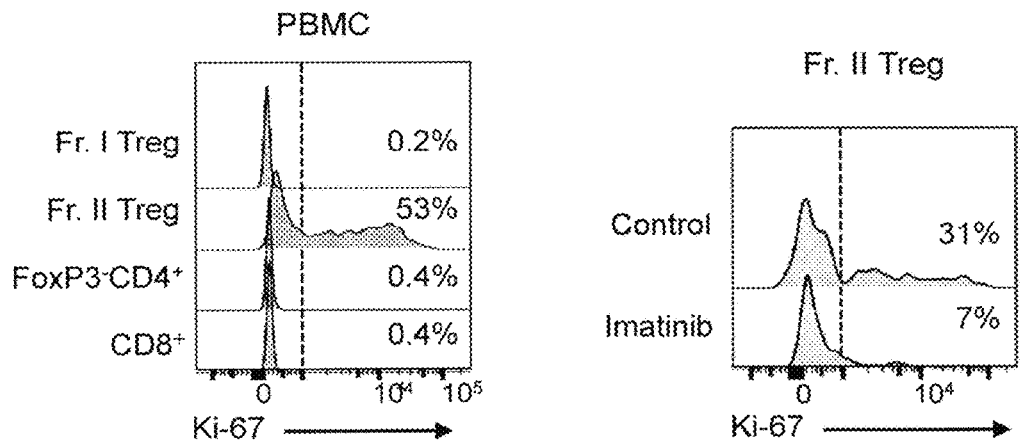
FIG. 17 shows the results of measurement of the expression levels of Ki-67 in the various T cells in Test Example 15, wherein the results of measurement of the expression levels of Ki-67 in the various cells isolated from peripheral blood are shown at the left, and the results of measurement of the expression level of Ki-67 in CD45RA$^-$FoxP3$^{high}$ cells (fraction II: effector Tregs) cultured in the presence of imatinib are shown at the right.

The results are shown in FIG. 17. In FIG. 17, the results of measurement of the expression levels of Ki-67 in the various cells isolated from the peripheral blood are shown at the left, and the results of measurement of the expression level of Ki-67 in CD45RA$^-$FoxP3$^{high}$ cells (fraction II: effector Tregs) cultured in the presence of imatinib are shown at the right. These results revealed that CD45RA$^-$FoxP3$^{high}$ cells (fraction II: effector Tregs) are much more proliferative in a normal state (PBMCs) than CD8$^+$ T cells, CD45RA$^+$FoxP3$^{low}$ cells (fraction I: naive Tregs), and FoxP3$^-$CD4$^+$ T cells, and the highly proliferative CD45RA$^-$FoxP3$^{high}$ cells (fraction II: effector Tregs) are selectively reduced when cultured in the presence of imatinib.

Test Example 16

The effector Treg cell apoptosis-inducing effect of imatinib was investigated. Initially, CD8$^+$ T cells, CD45RA$^+$FoxP3$^{low}$ cells (fraction I: naive Tregs), CD45RA$^-$FoxP3$^{high}$ cells (fraction II: effector Tregs), and FoxP3$^-$CD4$^+$ T cells were fractionated from the peripheral blood collected from a healthy donor, as in Test Example 13. T cells of each of the fractions were cultured for 4 days in RPMI1640 medium containing magnetic beads covalently bound to anti-CD3/anti-CD28 antibodies in a ratio of 1:1, and containing 10 μM of imatinib (Gleevec; Novartis Pharma K.K.; active ingredient: imatinib mesylate). After the culture, the activation level of Caspase 3/7 in T cells of each fraction was measured using CellEvent Caspase 3/7 green and SYTOX AAD-vanced. As a control, the same test as described above was performed, except that the medium not containing imatinib was used, and the activation level of Caspase 3/7 was measured.

Figure 18:
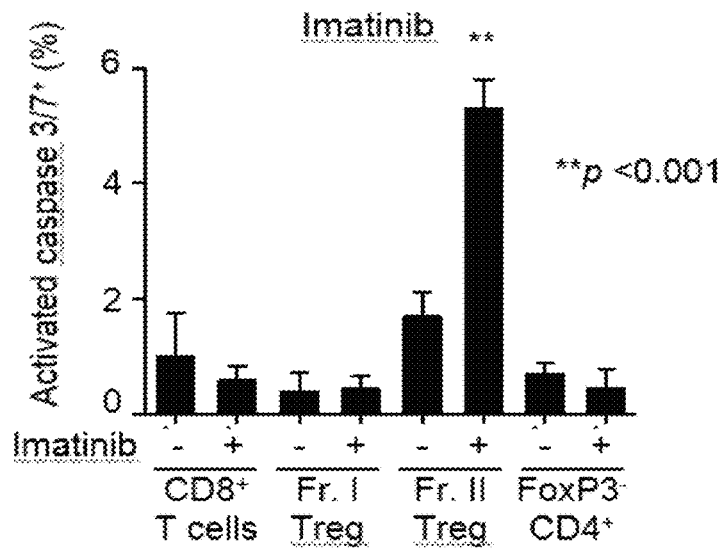
FIG. 18 shows the results of measurement of the activation levels of caspase 3/7 in CD8$^+$ T cells, CD45RA$^+$FoxP3$^{low}$ cells (fraction I: naive Tregs), CD45RA$^-$FoxP3$^{high}$ cells (fraction II: effector Tregs), and FoxP3$^-$CD4$^+$ cells derived from the peripheral blood of a healthy donor, cultured with imatinib under stimulation with anti-CD3 antibody and anti-CD48 antibody in Test Example 17.

The results are shown in FIG. 18. In FIG. 18, the vertical axis represents the proportion (%) of T cells having activated Caspase 3/7. These results revealed that imatinib activates Caspase 3/7 in a CD45RA$^-$FoxP3$^{high}$ cell (fraction II: effector Tregs)-specific manner to induce apoptosis.

Test Example 16

The activation of cancer antigen-specific immune responses elicited by imatinib was investigated in vitro, using human peripheral blood mononuclear cells derived from a patient with gastric cancer. Initially, human peripheral blood mononuclear cells derived from the patient with gastric cancer were cultured for 1 day in RPMI1640 medium containing 5 μM of imatinib (Gleevec; Novartis Pharma K.K.; active ingredient: imatinib mesylate), 10 IU/mL of IL-2, and 20 ng/mL of IL-7, and subsequently, testis antigen (HLA-Cw*0304-restricted NY-ESO-1 peptide p92-100 (LAMPFATPM)) was added at a concentration of 10 μg/mL into the medium to start antigen stimulation with NY-ESO-1 peptide. Three days after the start of antigen stimulation, the medium was replaced with RPMI1640 medium containing 5 μM of imatinib, 10 IU/mL of IL-2, 20 ng/mL of IL-7, and 10 μg/mL of cancer/testis antigen (HLA-Cw*0304-restricted NY-ESO-1 peptide p92-100 (LAMPFATPM)), and the cells were cultured for 6 days from the start of antigen stimulation. After the culture, the cells were harvested, and NY-ESO-1-specific CD8$^+$ T cells were detected using the HLA-Cw*0304 NY-ESO-1 tetramer method. As a control, the same test as described above was performed, except that the medium not containing imatinib was used, and NY-ESO-1-specific CD8$^+$ T cells were detected.

Figure 19:
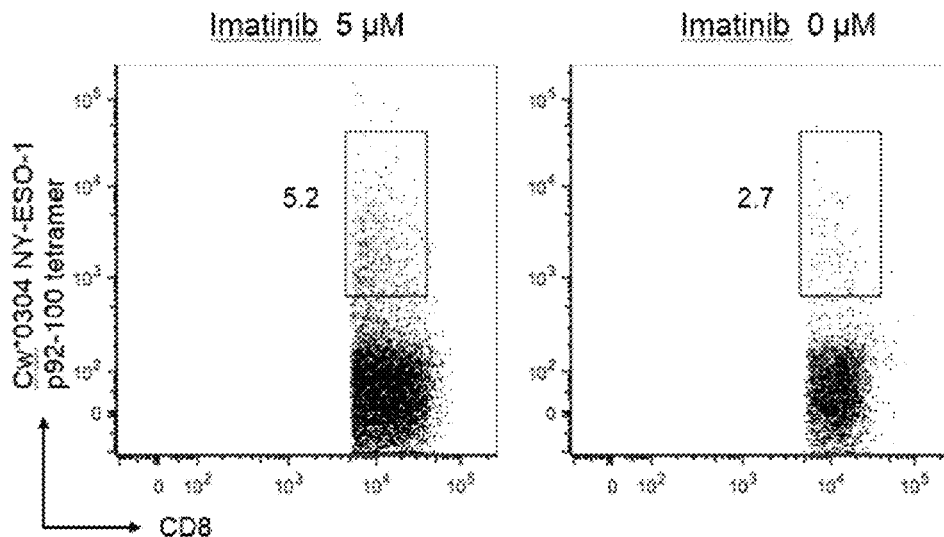
FIG. 19 shows the results of detection of cancer antigen-specific CD8$^+$ T cells after cancer antigen-specific stimulation of human peripheral blood mononuclear cells derived from a patient with gastric cancer, in the presence or absence of imatinib, in Test Example 18.

The results are shown in FIG. 19. These results revealed that imatinib has the action of potentiating the induction of cancer antigen (NY-ESO-1)-specific CD8$^+$ T cells from human peripheral blood mononuclear cells derived from a patient with gastric cancer.

Test Example 17

The activation of cancer antigen-specific immune responses elicited by imatinib was investigated in vitro, using human peripheral blood mononuclear cells derived from a patient with ovarian cancer. The specific testing method was the same as described in Test Example 16 above, except that human peripheral blood mononuclear cells derived from the patient with ovarian cancer were used instead of human peripheral blood mononuclear cells derived from the patient with gastric cancer.

Figure 20:
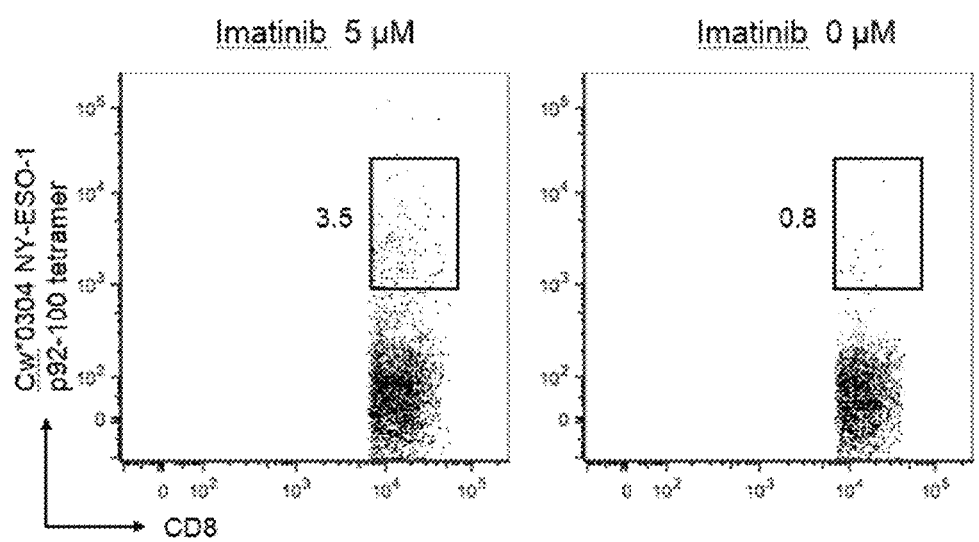
FIG. 20 shows the results of detection of cancer antigen-specific CD8$^+$ T cells after cancer antigen-specific stimulation of human peripheral blood mononuclear cells derived from a patient with ovarian cancer, in the presence or absence of imatinib, in Test Example 19.

The results are shown in FIG. 20. These results confirmed that imatinib also has the action of potentiating the induction of cancer antigen (NY-ESO-1)-specific CD8$^+$ T cells from human peripheral blood mononuclear cells derived from a patient with ovarian cancer.

The invention claimed is:

1. A method of treating a chronic myelogenous leukemia in a subject in need thereof, the method comprising:

administering to the subject an immunopotentiating agent comprising imatinib and/or a salt thereof as an active ingredient, and administering to the subject Melan-A antigen, wherein the Melan-A antigen is administered subsequent to administering the immunopotentiating agent, wherein there is a reduction in number of effector Tregs in the peripheral blood of the subject and wherein there is an increase in the number of CD8$^+$ T cells specific to the antigen specific to chronic myelogenous leukemia, so that immunity against the chronic myelogenous leukemia in the subject is potentiated.

2. The method of claim 1, further comprising:

counting regulatory T cells contained in peripheral blood collected from the subject with chronic myelogenous leukemia after receiving administration of the imunopotentiating agent and the Melan-A antigen, and predicting therapeutic efficacy of the administering of the imunopotentiating agent and the Melan-A antigen based on the number of the regulatory T cells.

3. The testing method according to claim 2, wherein effector regulatory T cells contained in the peripheral blood are counted, and the therapeutic efficacy of the administering of the imunopotentiating agent and the Melan-A antigen is predicted based on the number of the effector regulatory T cells.

4. The testing method according to claim 2, wherein the testing method is for predicting whether a molecular genetic complete response will be achieved or not.

* * * * *